United States Patent
Chambers et al.

(10) Patent No.: US 12,144,492 B2
(45) Date of Patent: Nov. 19, 2024

(54) MOUTHPIECE AND ATTACHMENT

(71) Applicant: ONARIA TECHNOLOGIES LTD., London (GB)

(72) Inventors: Oliver Henry Sherston Chambers, London (GB); Ian Dera, London (GB); Clara Gaggero, London (GB); Adrian Lucien Reginald Westaway, London (GB)

(73) Assignee: Onaria Technologies Ltd., London (GB)

( * ) Notice: Subject to any disclaimer, the term of this patent is extended or adjusted under 35 U.S.C. 154(b) by 341 days.

(21) Appl. No.: 17/764,336

(22) PCT Filed: Sep. 25, 2020

(86) PCT No.: PCT/GB2020/000076
§ 371 (c)(1),
(2) Date: Mar. 28, 2022

(87) PCT Pub. No.: WO2021/058930
PCT Pub. Date: Apr. 1, 2021

(65) Prior Publication Data
US 2022/0338727 A1  Oct. 27, 2022

(30) Foreign Application Priority Data
Sep. 26, 2019 (GB) .................................... 1913863

(51) Int. Cl.
*A61B 1/32* (2006.01)
*A61B 1/24* (2006.01)

(52) U.S. Cl.
CPC .................. *A61B 1/32* (2013.01); *A61B 1/24* (2013.01)

(58) Field of Classification Search
CPC ..................................... A61B 1/32; A61B 1/24
See application file for complete search history.

(56) References Cited

U.S. PATENT DOCUMENTS

| 10,796,597 B1 * | 10/2020 | Tanaka ................. G06F 1/1632 |
| 2018/0303580 A1 | 10/2018 | Salah et al. |
| 2019/0167115 A1 | 6/2019 | Dorodvand et al. |

FOREIGN PATENT DOCUMENTS

WO    2016185463 A1    11/2016

OTHER PUBLICATIONS

Corresponding International Patent Application No. PCT/GB2020/000076, International Search Report and Written Opinion, mailed Jan. 19, 2021.

* cited by examiner

*Primary Examiner* — Sameh R Boles
(74) *Attorney, Agent, or Firm* — Cooper Legal Group LLC

(57) ABSTRACT

A mouthpiece for attachment to an imaging device comprises a tubular body having a first end and a second end, both ends being open, and a band of flexible material attached to the first end of the body. The band comprises an opposing portion opposite the first end of the body. It may also comprise one or more adjacent portions, connected to the first end of the body and parallel to the opposing portion.

17 Claims, 6 Drawing Sheets

MOUTHPIECE AND ATTACHMENT

CROSS REFERENCE TO RELATED APPLICATIONS

This application claims priority from UK Patent Application No. 19 13 863.5, filed on Sep. 26, 2019, which is incorporated herein by reference.

BACKGROUND OF THE INVENTION

The present invention relates to a mouthpiece for attachment to an imaging device.

Mouthpieces may be attached to imaging devices to obtain images of the teeth. For healthcare professionals, an attachment may be provided for a camera, and often this is permanently attached. However, more recently, it has been suggested to attach a mouthpiece to a mobile telephone, so that a person may obtain images of their own teeth.

Methods of attaching a mouthpiece to an imaging device include clips, screw fits, push fits, and so on. The need to keep the mouthpiece in a fixed position relative to the device while obtaining an image, means that many of these attachment means are bulky, and potentially not suitable for use across a wide variety of devices.

It is therefore an object of the invention to provide an improved means for attaching a mouthpiece to an imaging device.

BRIEF SUMMARY OF THE INVENTION

According to a first aspect of the present invention, there is provided a mouthpiece for attachment to an imaging device, comprising: a tubular body having a first end and a second end, both ends being open; and a band of flexible material attached to said first end of said body, comprising an opposing portion opposite said first end of said body.

According to a second aspect of the present invention, there is provided a method of manufacturing a mouthpiece, comprising the steps of: manufacturing a tubular body having a first end and a second end, both ends being open; and manufacturing a band of flexible material attached to said body, said band comprising an opposing portion opposite said first end of said body.

Embodiments of the invention will be described, by way of example only, with reference to the accompanying drawings. The detailed embodiments show the best mode known to the inventor and provide support for the invention as claimed. However, they are only exemplary and should not be used to interpret or limit the scope of the claims. Their purpose is to provide a teaching to those skilled in the art. Components and processes distinguished by ordinal phrases such as "first" and "second" do not necessarily define an order or ranking of any sort.

DETAILED DESCRIPTION OF EMBODIMENTS OF THE INVENTION

FIG. 1

Figure 1:
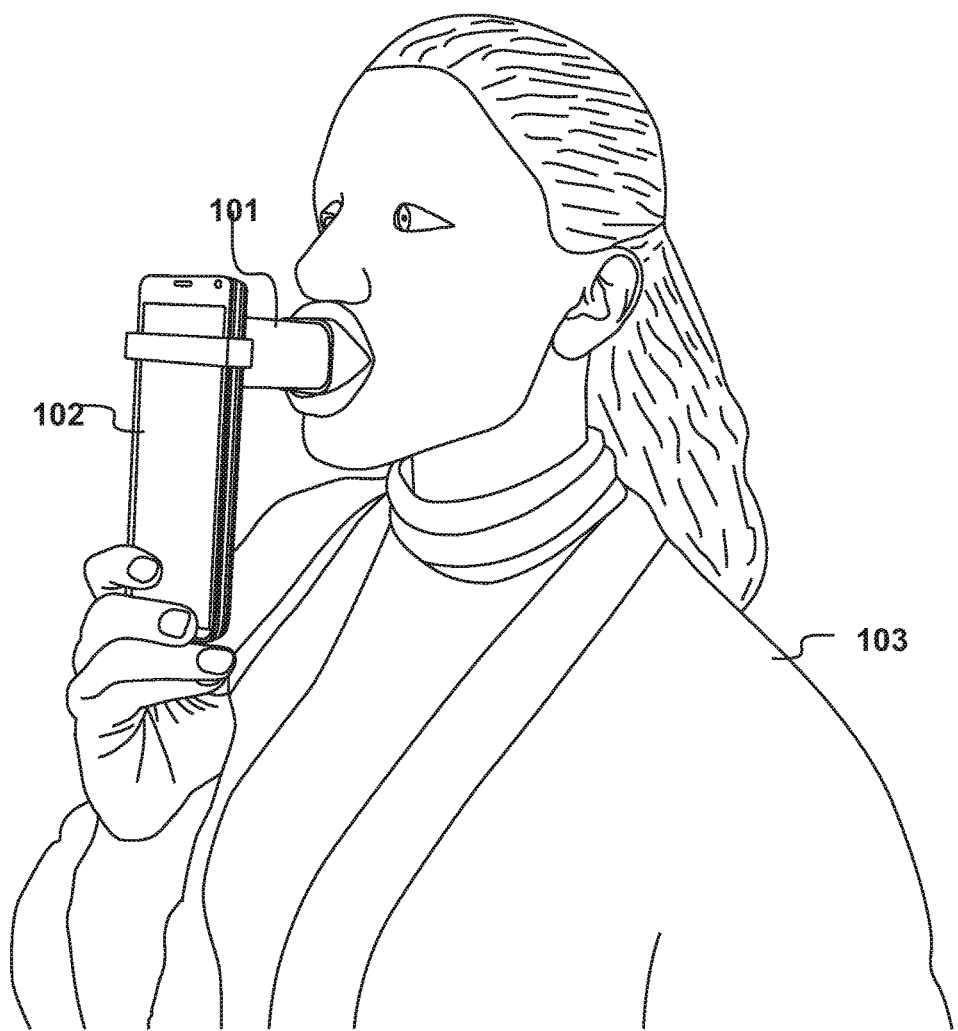
FIG. 1 shows a user obtaining images of their teeth using a mobile device and a mouthpiece.

In FIG. 1, a mouthpiece 101 is attached to a mobile device 102, which in this example is a mobile telephone, allowing user 103 to obtain an image of their teeth and gums.

Mouthpiece 101 is attached to telephone 102 in such a way that very little ambient light enters the mouthpiece. The other end of the mouthpiece is held in the user's mouth against the teeth and gums, and again the seal provided by the lips prevents ambient light entering the mouthpiece. The teeth can therefore be imaged under only the white light from the device, usually provided by the camera flash or torch. Mouthpiece 101 can be easily removed from device 102 and replaced in the same position, allowing user 103 to obtain consistent images of their teeth on a regular basis. These images may then be analysed to show changes in the user's mouth over time, for example whether plaque or gingivitis is worsening or getting better.

It is therefore important that the mouthpiece 101 be placed in a reproducible position on device 102. However, this has proved difficult using previous means of attaching mouthpieces, due to the need to accommodate many different sizes of device. In today's market, the width of a smartphone may be anything from fifty-five centimetres to eighty centimetres, while its depth could be between seven centimetres and nine centimetres. This wide variety of sizes is likely to continue, as many users prefer a smaller mobile telephone despite the continuing trend for larger screen sizes. The matter is further complicated in that many users prefer to use cases for their devices.

Even when a mouthpiece is designed to fit only onto a small range of devices, the necessity for the seal between the mouthpiece and the device to be substantially light-proof has in the past caused difficulties in designing attachment means.

FIG. 2

Figure 2:
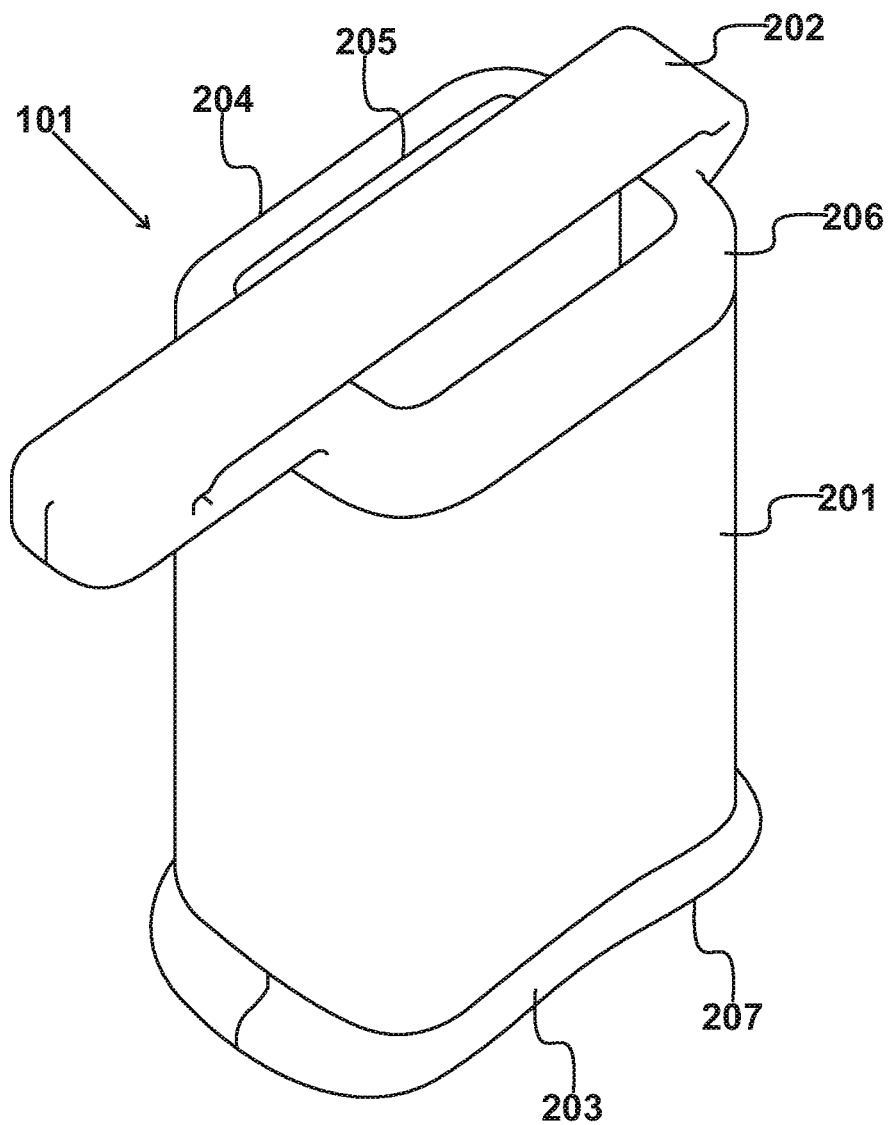
FIG. 2 illustrates the mouthpiece shown in FIG. 1.
Figure 3:
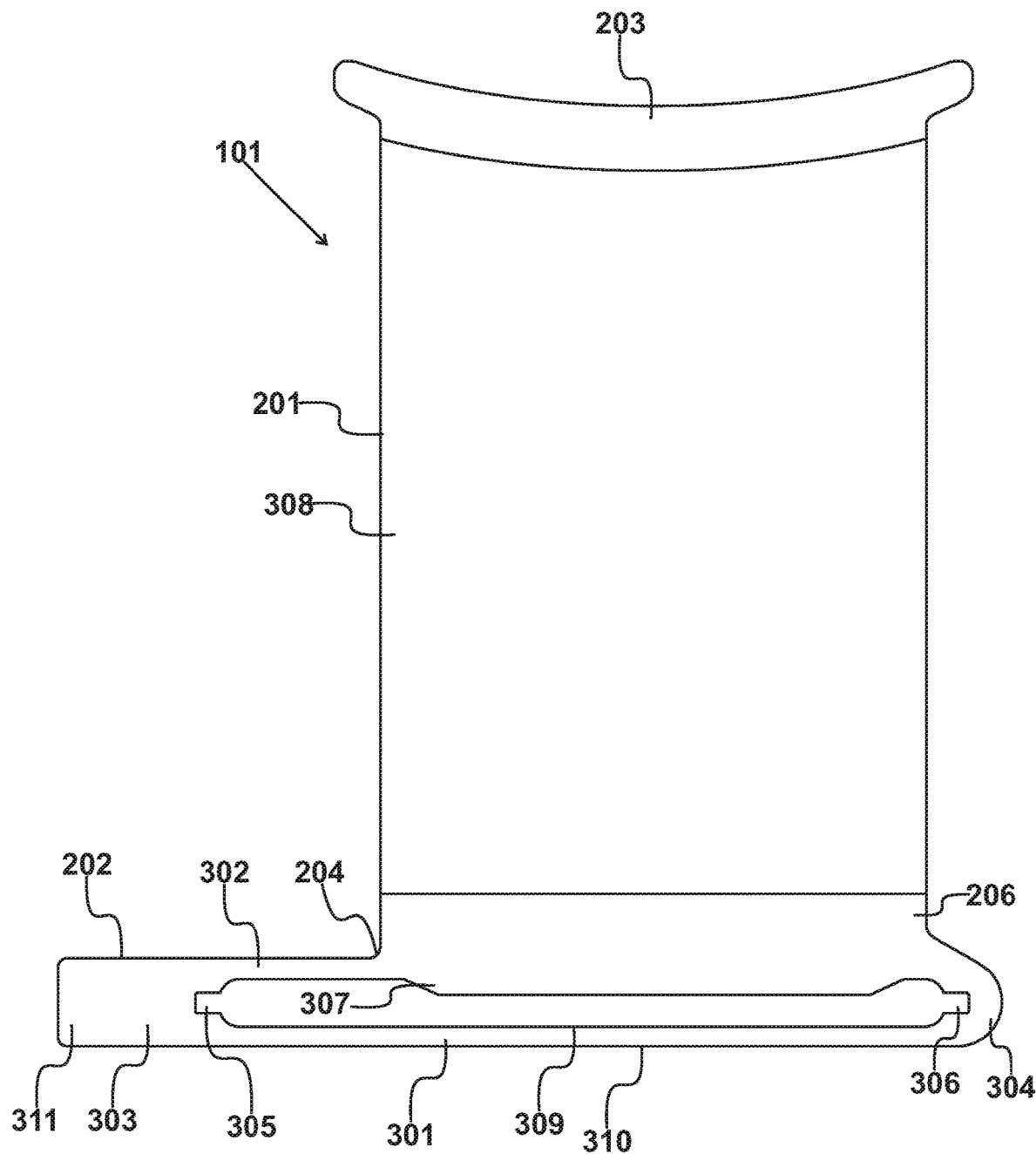
FIG. 3 is a side view of the mouthpiece shown in FIG. 1.

Mouthpiece 101 is shown in FIG. 2, and will be shown again in side view in FIG. 3. It comprises a tubular body 201, a flexible continuous band 202, and a rim 203. Tubular body 201 has two open ends. First end 204 has an opening 205 covered with edging portion 206. Edging portion 206 is integral with band 202. The second end 207 has rim 203 running around it, which is designed to be placed in the user's mouth.

In use, band 202 is placed over a smartphone or other imaging device, such that the lens and flash of the device are visible from end 207 through opening 205. The user may adjust band 202 until the mouthpiece is in the right position. The user then places rim 203 in their mouth and takes a photograph using the camera app on the device.

In this embodiment, tubular body has a cross-section that is substantially rectangular with rounded corners. However, other shapes, including irregular shapes, could be used.

FIG. 3

A side view of mouthpiece 101 is shown in FIG. 3.

Band 202 is made from a flexible and elastic material. It has a wide, flat profile, such that its inner surface 309 and outer surface 310 are substantially parallel to each other. The band is approximately 14 mm wide (in the direction away from the viewer in FIG. 3) and 1.5 mm deep (between surfaces 309 and 310). This shape has been found to facilitate the best attachment to a mobile device, with the flat, wide inner surface providing a friction fit against the surface of a device, while retaining enough flexibility to be placed over the device. However, in other embodiments the band may have another size or shape.

Band 202 comprises an opposing portion, which in this example is lower portion 301, that is opposite and parallel to the edges of first end 204. Lower portion 301 is intended, in use, to be in contact with the screen of a device. Band 202 also includes a first adjacent portion, which in this example is upper portion 302, which is parallel to lower portion 301. Upper portion 302 and lower portion 301 are connected by first joining portion 303, which is designed to go around the edge of a device. Upper portion 302 is attached to and integral with edging portion 206, which defines opening 205. At the other end of lower portion 301, second joining portion 304 is attached to and integral with edging portion 206.

Thus, in this embodiment, tubular body 201 is offset with regard to band 202, rather than central. In other embodiments, there could be a second adjacent portion on the other side of the body from upper portion 302, In such an embodiment with two adjacent portions, they may be of the same length or of differing lengths. As a further alternative, there could be no adjacent portions, with both sides of the first end of the body connected directly to joining portions and thereby to the opposing portion.

In further alternative embodiments, either or both of the joining portions, which in this embodiment bulge outwards from tubular body 201, could have an edge that is in a line with body 201.

Therefore, tubular body could be centrally located with respect to band 202, or could be more offset or less offset. However, the arrangement shown in FIG. 3 has been found by the applicant to be the one that provides the most ease of use and reproducibility of position when attaching to a variety of sizes of mobile devices.

Figure 5:
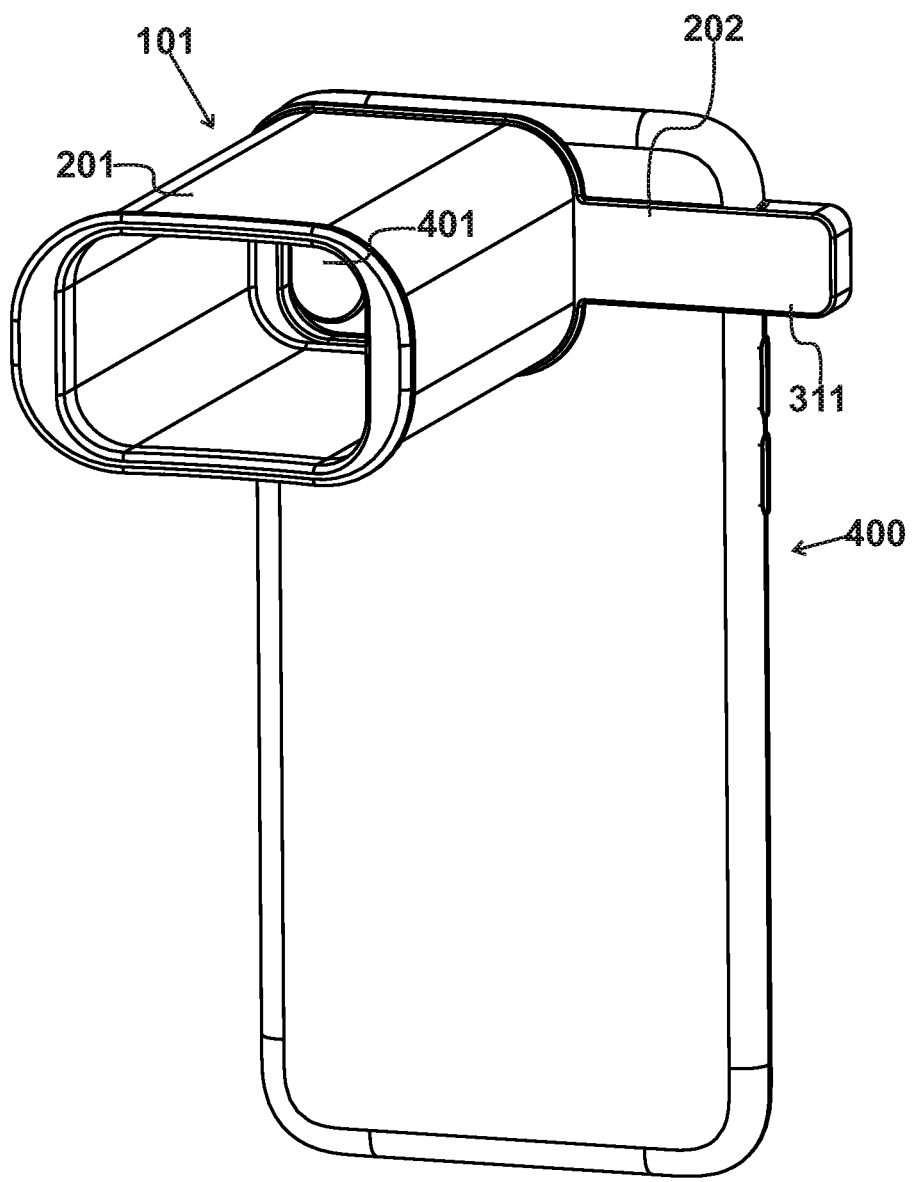
FIG. 5 illustrates the mouthpiece shown in FIG. 1 attached to the mobile device shown in FIG. 4.

Each joining portion 303 and 304 includes a small recess 305 and 306 respectively. These recesses are on the inside of the band and have a square profile. In use, these are designed to go over any buttons on the side of the mobile device, as will be described further with reference to FIG. 5.

First joining portion 303 includes a tab 309. This is an extension of band 202 that provides a holding location for a user. In this example it has the same width as the band, and is approximately 7.5 mm deep. By holding this tab, it is easier for the user to manoeuvre band 202 into the right position on a telephone. In other embodiments the tab may be of a different shape or size, or may be omitted.

Upstanding from edging portion 206 is a fin 307. This is a thin line of material that runs all the way around opening 205, and improves the light-proof seal when mouthpiece 101 is attached to a device. However, in other embodiments the fin may be omitted.

The visible part of tubular body 201 is an external part 308 made from a hard material that provides rigidity to the mouthpiece. A thermoplastic polymer such as ABS is suitable, as are many other plastics. Rim 203 is made from a soft material and has a concave curvature that is similar to the typical curvature of an adult's teeth, so that in use rim 203 sits against the teeth and gums in a comfortable, reproducible position.

Thus there is provided a mouthpiece 101 for attachment to an imaging device, comprising a tubular body 201 having a first end 204 and a second end 207, both ends being open, and a band 202 of flexible material attached to the first end, comprising an opposing portion 301 opposite the first end of the body.

FIG. 4

Figure 4:
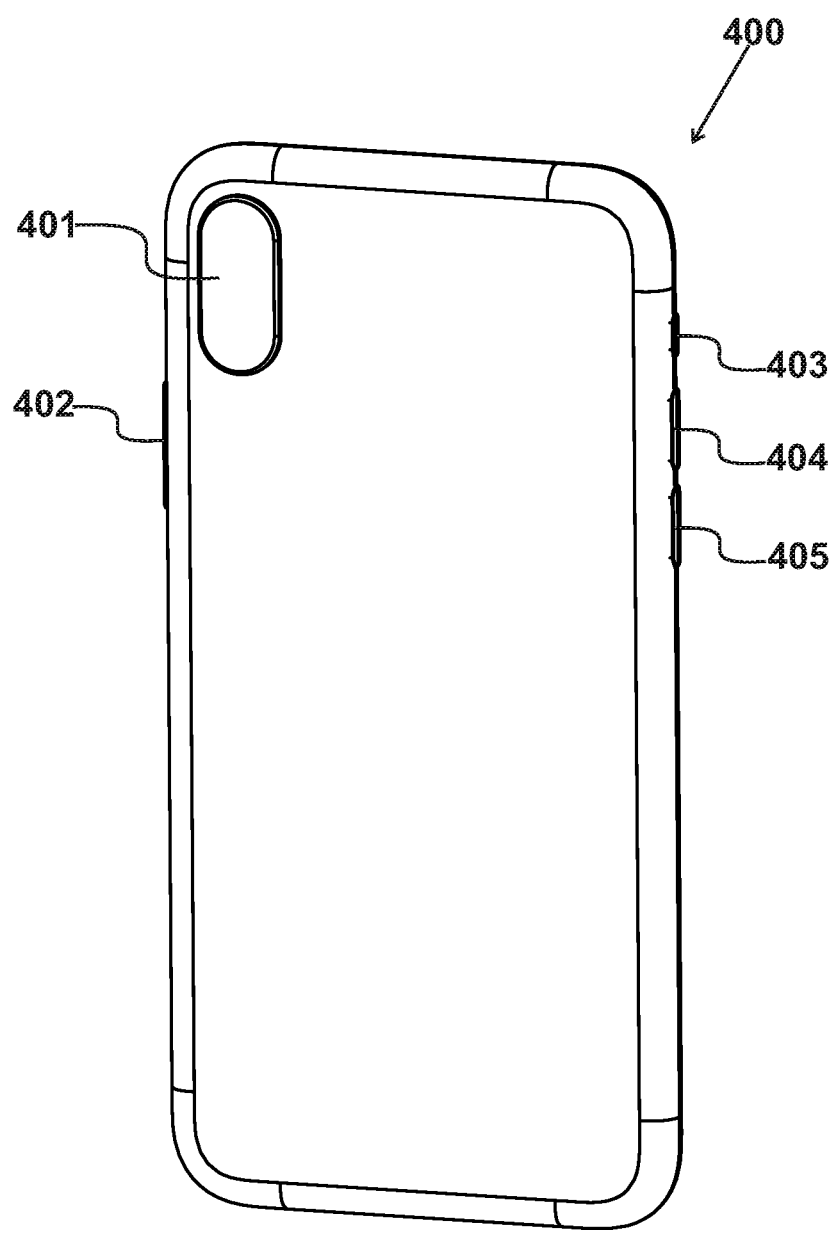
FIG. 4 illustrates the back of a mobile device.

A mobile device 400 is illustrated in FIG. 4. The back of the device is shown, with imaging unit 401 comprising a lens and flash, as is common on mobile telephones. In this example, the imaging unit 401 is at the edge of the device. However, other smartphones may have the imaging unit centrally. In addition, while the imaging units are normally towards the top of the phone, they are sometimes at the very top as shown here and sometimes further down. In addition to the varying sizes of mobile devices, the varying positions of the imaging units presents a challenge when designing attachment means for a mouthpiece.

A further issue are the buttons commonly found on the side of mobile devices. In this example, the device has one button 402 on the side closest to camera unit 401, and three buttons 403, 404 and 405 down the other side. Typical smartphones will have at least three buttons, for power and volume (although the two volume buttons may be integrated into a single rocker). Some telephones, like the one shown here, have a fourth button, which may for example trigger a voice-activated software assistant. On some mobile devices there are no buttons exactly in line with the imaging unit, but on others there are buttons level with the imaging unit on one or both sides. It is important that when band 202 is around the mobile phone, it does not press on any of these buttons. Therefore, recesses 305 and 306 are provided in band 202 to locate over any buttons. Placement of a recess over a button may also provide an anchoring effect, preventing the band from slipping. In this embodiment recesses have a square profile, but any suitable shape may be used, for example rectangular, semi-circular, and so on.

In still further embodiments these recesses may be omitted from the band, particularly if it is found in practice that the band does not press on any buttons sufficiently to activate them.

FIG. 5

Mouthpiece 101 is placed over mobile device 400 so that imaging unit 401 can be seen through tubular body 201. Due to the flexible and elastic nature of band 202 it can easily be fitted over any mobile device and placed into position. Adjustments can be assisted by the user grasping tab 309 to pull band 202 away from device 400, making it easier to position tubular body 201 over imaging unit 401.

On mobile telephones where the imaging unit is lower down, the mouthpiece can easily be placed in a different vertical position. On telephones where the imaging unit occupies a more central position, the elasticity of band 202 allows tubular body 201 to be placed in a more central position, while still ensuring that any buttons on the side of the telephone are within recess 305 or 306. This is the case shown in FIG. 1, when the mouthpiece 101 is attached to mobile telephone 102, which has a lower down and more central imaging unit.

The choice of material for band 202 is important. In this embodiment, it should be flexible and elastic enough to allow such adjustment of the mouthpiece. However, if it is too elastic or too soft then the weight of tubular body 201 will tend to pull the mouthpiece away from the device, potentially compromising the light-proof seal required. A suitable material is a thermoplastic elastomer, such as styrenic block copolymers, thermoplastic polyolefinelastomers, thermoplastic vulcanizates, thermoplastic copolyester elastomers, thermoplastic polyamides, and other thermoplastic elastomers. Other suitable materials may be used.

In other embodiments, where the mouthpiece is designed to fit a smaller variety of devices, the band need not be elastic and need only be flexible.

In both cases, the hardness of the material needs to be carefully selected. A Shore A hardness of around 60 has been found to be suitable, although materials having another hardness, potentially from 20 to 90, could be used.

FIG. 6

Figure 6:
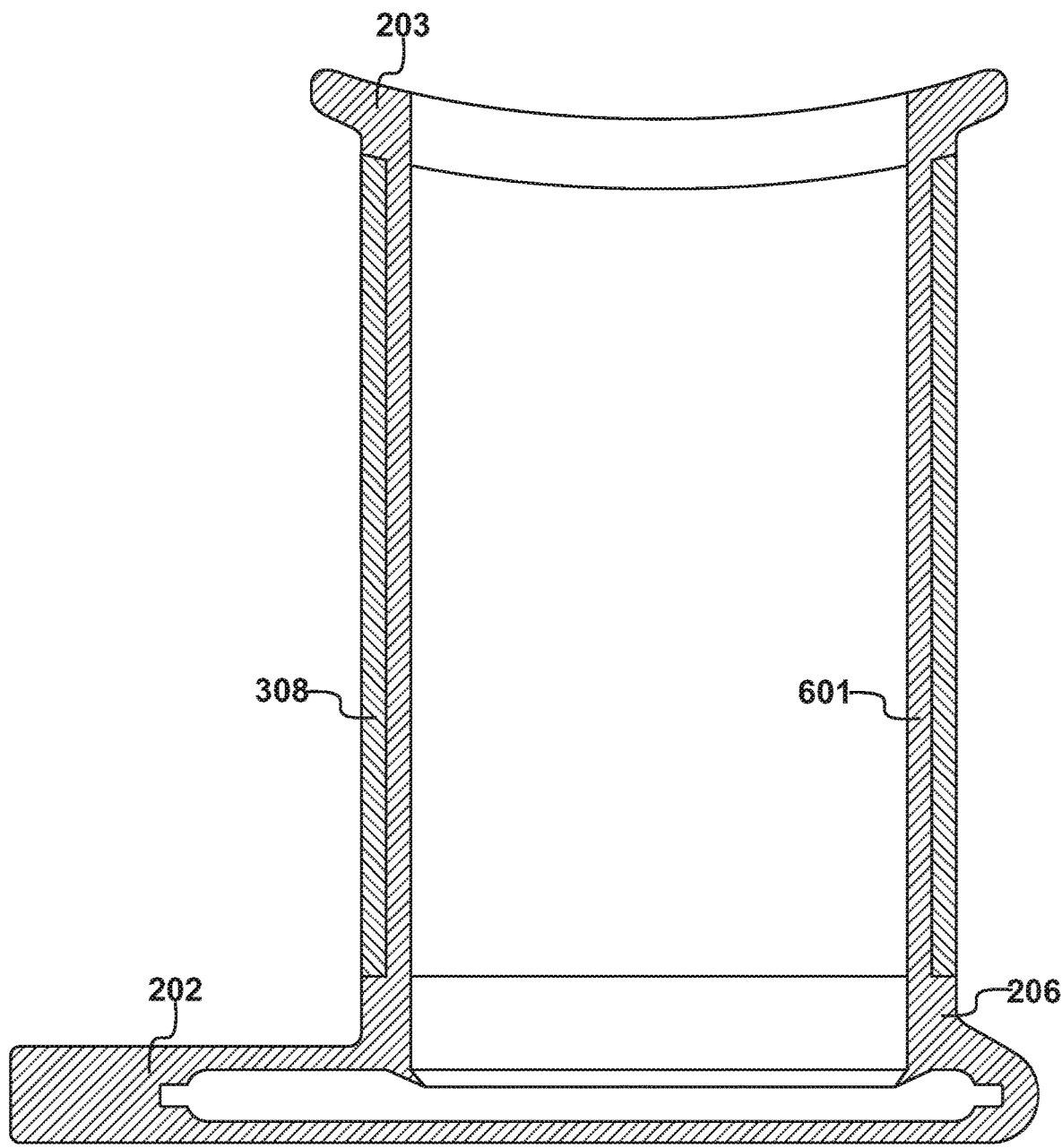
FIG. 6 is a cross section of the mouthpiece shown in FIG. 1.

Mouthpiece 101 is shown in cross-section in FIG. 6. In this example, the mouthpiece is formed using a two-shot moulding process. The band 202, rim 203, flexible portion 206 and an internal portion 601 of the tubular body are all integrally moulded in one piece from the same material. The hard external portion 308 of the tubular body is then moulded over the top.

This method of manufacture is relatively inexpensive and produces a robust end product. It is possible because the material used for band 202 is also suitable for rim 203, which is to held in the user's mouth against the teeth and gums. However, the mouthpiece may be manufactured using other methods. In particular, if the rim were to be made of a different material, then it would be more suitable to make the mouthpiece in three portions, the rim, the tubular body, and the band, and attach them all together, for example in an over-moulding process.

In this embodiment the thickness of the tubular body 201 does not vary along its length, nor does its width. However, in other embodiments the width or wall thickness could be varied in order to provide a tapering effect, so that the opening of the body at the device end is narrower than the opening at the mouth end. This can assist with obtaining images under some conditions.

The invention claimed is:

1. A mouthpiece for attachment to an imaging device, comprising:
    a tubular body having a first end and a second end, said first end and said second end being open; and
    a band of flexible material attached to said first end of said tubular body, said band comprising an opposing portion opposite said first end of said tubular body,
    wherein said band further comprises a first adjacent portion, which is joined at one end to said first end of said tubular body, and is substantially parallel to said opposing portion,
    wherein the other end of said first adjacent portion is joined by a first joining portion to one end of said opposing portion, and
    wherein said first joining portion has a recess on an inside of said band, sized to fit over a button on a side of a mobile telephone.

2. The mouthpiece according to claim 1, wherein said opposing portion has an inner surface substantially parallel to edges of said first end of said tubular body.

3. The mouthpiece according to claim 1, wherein one end of said opposing portion is joined by a second joining portion to said first end of said tubular body.

4. The mouthpiece according to claim 1, further comprising a second adjacent portion, which is joined at one end to said first end of said tubular body, is substantially parallel to said opposing portion, and is joined by a second joining portion to one end of said opposing portion.

5. The mouthpiece according to claim 4, wherein said first adjacent portion and said second adjacent portion have different lengths.

6. The mouthpiece according to claim 1, wherein said band has a flat profile with parallel inner and outer surfaces.

7. The mouthpiece according to claim 1, wherein said first joining portion comprises a tab of material extending away from ends of said opposing portion and said first adjacent portion.

8. The mouthpiece according to claim 7, wherein said tab is made of the same material as said band and is integral with said band.

9. The mouthpiece according to claim 8, wherein said tab has a substantially cuboid shape.

10. The mouthpiece according to claim 1, wherein said band is made from an elastic material.

11. The mouthpiece according to claim 1, wherein said mouthpiece further comprises a fin of deformable material around an edge of said first end and extending away from said first end.

12. The mouthpiece according to claim 11, wherein said fin is made from the same material as said band and is integral with said band.

13. The mouthpiece according to claim 1, wherein said tubular body is made in two parts, with an internal part being made from the same material as said band and an outer part being made from a hard material.

14. The mouthpiece according to claim 13, wherein said band, said internal part of said tubular body and a rim of said mouthpiece are integral.

15. A method of manufacturing a mouthpiece, comprising the steps of:
    manufacturing a tubular body having a first end and a second end, said first end and said second end being open; and
    manufacturing a band of flexible material attached to said first end of said tubular body, said band comprising an opposing portion opposite said first end of said tubular body,
    wherein said band further comprises a first adjacent portion, which is joined at one end to said first end of said tubular body, and is substantially parallel to said opposing portion,
    wherein the other end of said first adjacent portion is joined by a first joining portion to one end of said opposing portion, and
    wherein said first joining portion has a recess on an inside of said band, sized to fit over a button on a side of a mobile telephone.

16. The method of manufacturing a mouthpiece according to claim 15, further comprising the step of:
    manufacturing a tab attached to said band.

17. The method of manufacturing a mouthpiece according to claim 15, wherein:
    said tubular body is formed in two parts, an internal part and an external part; and
    said steps of manufacturing said tubular body and said band comprise the steps of:
    moulding, from said flexible material, a first part comprising said band, said internal part of said tubular body, and a rim around said second end of said tubular body; and
    moulding, from a hard material, said external part of said tubular body.

* * * * *